United States Patent [19]

Eichman et al.

[11] 4,013,792

[45] Mar. 22, 1977

[54] PROCESS FOR THE PRODUCTION OF BASE FOR TOPICAL STEROIDS

[75] Inventors: Martin L. Eichman, Wilmington, Del.; Susan C. Belsole, Chester, N.J.

[73] Assignee: Warner-Lambert Company, Morris Plains, N.J.

[22] Filed: Sept. 18, 1975

[21] Appl. No.: 614,386

Related U.S. Application Data

[63] Continuation-in-part of Ser. No. 460,254, April 11, 1974, abandoned.

[52] U.S. Cl. .............................. 424/181; 424/243; 424/362
[51] Int. Cl.² ................. A61K 31/56; A61K 31/71
[58] Field of Search ................... 424/181, 243, 362

[56] References Cited

UNITED STATES PATENTS

| | | | |
|---|---|---|---|
| 3,485,915 | 12/1969 | Gerstein et al. | 424/362 X |
| 3,529,060 | 9/1970 | Ercoli et al. | 424/243 |
| 3,749,773 | 7/1973 | Ninger et al. | 424/81 |

*Primary Examiner*—Albert T. Meyers
*Assistant Examiner*—Allen J. Robinson
*Attorney, Agent, or Firm*—Albert H. Graddis; Frank S. Chow; Anne M. Kelly

[57] ABSTRACT

A clear gel composition containing a topically active anti-inflammatory steroid and a neomycin salt is disclosed. The clear gel composition is prepared by dissolving the steroid in a polyhydroxy alcohol/lower alcohol solvent, a major proportion of the polyhydroxy alcohol solvent being propylene glycol, and adding a hydroxycellulose ingredient; an aqueous solution of the neomycin salt is then added to the steroid formulation and, upon the addition of an alkali metal chloride salt, such as sodium chloride, a clear gel is obtained. The pH may be adjusted to 4–5. The resulting composition is indicated for the relief of corticosteroid-responsive dermatoses.

1 Claim, No Drawings

PROCESS FOR THE PRODUCTION OF BASE FOR TOPICAL STEROIDS

This application is a continuation-in-part of our co-pending application Ser. No. 460,254, filed Apr. 11, 1974, now abandoned.

The present invention relates to a process for the production of a base particularly suitable for the incorporation of topically active steriods and a topically active anti-microbial agent. Among the topically active steroids which may be included in this base are, for example, triamcinolone acetonide, fluocinolone acetonide, betamethasone 17-valerate, betamethasone 17-benzoate, dexamethasone and the like. Betamethasone 17-valerate, betamethasone 17-benzoate, and dexamethasone are the preferred anti-inflammatory steroids for use in this invention. A particularly preferred embodiment of the invention involves a process for preparing a clear gel composition containing betamethasone 17-benzoate (17α-benzoyloxy-9α-fluoro-16β-methyl-$\Delta^{1,4}$-pregnadiene-11β,21-diol-3,20-dione) and a salt of neomycin, typically neomycin sulfate.

Also encompassed within the scope of this invention are the resulting topically active active compositions containing at least one of the above-mentioned anti-inflammatory steroids and the antimicrobial agent.

The use of topically active steroids to treat local inflammatory conditions is a well-accepted therapeutic procedure. Generally, the steroid is suspended or dissolved in a base for application to the inflamed site. In instances where inflammation is complicated by bacterial infections, a topically active antimicrobial agent is combined with the steroid to combat bacterial infections.

Betamethasone 17-benzoate is newly discovered topical steroid. The preparation of this compound is described in British Specification No. 1,191,965 published Sept. 16, 1970, Japanese Pat. No. 983,947 published Sept. 22, 1970, Swedish Pat. No. 330,538 published Apr. 15, 1971, South African Pat. No. 681,303 published Feb. 4, 1969, French Pat. No. M-8027 published June 22, 1970, German Pat. No. 1668858, published July 12, 1972, and U.S. Pat. No. 3,529,060, published Sept. 15, 1970.

In order to provide maximum topical activity for the betamethasone 17-benzoate, a novel ointment base was produced. This forms the basis of British Complete Specification No. 1,316,556 issued Feb. 11, 1972, pending Japanese Application No. 47-019022 filed Feb. 25, 1972, pending German Application No. 2207294.2 filed Feb. 16, 1972 and U.S. Pat. No. 3,749,773 issued July 31, 1973. Briefly, the gel base disclosed comprises ethanol, propylene glycol, gelled by the incorporation of a carboxy vinyl polymer neutralized with an amine. This forms a clear gel with the betamethasone 17-benzoate and is suitable for use with the other topically active anti-inflammatory steroids mentioned above. The clear gel composition is applied topically and permits maximum absorption of the steroids. However, when such a base containing the anti-inflammatory steroid is used to include an antimicrobial agent such as neomycin sulfate, a coagulated precipitate forms. This is obviously undesirable. Moreover, in actual microbiological assay by the standard agar cup method, there was no available neomycin sulfate to provide the desired antimicrobial activity.

We have now discovered a process for preparing a new base suitable for the incorporation of at least one of the aforementioned topically active anti-inflammatory steroids with a salt of neomycin. Broadly speaking, this base is produced by first dissolving from about 0.005% to about 0.05% by weight, preferably about 0.025% by weight of the topically active anti-inflammatory steroid in a polyhydroxy alcohol/lower alcohol solvent combination which contains from about 20% to about 60% by weight of the polyhydroxy alcohol solvent and from about 3% to about 25% by weight of the lower alcohol solvent. The polyhydroxy alcohols used as solvents in this invention are those which contain two or three hydroxy groups, generally known as diols or glycols, and triols. At least from about 20% to about 45% by weight of the polyhydroxy alcohol solvent must be propylene glycol; other suitable polyhydroxy alcohol solvents, which may optically be admixed with the propylene glycol solvent, include glycerin, ethylene glycol, butylene glycol, and the like. The lower alcohol solvent may be isopropyl alcohol, ethyl alcohol or the like. A preferred solvent for the anti-inflammatory steroid contains about 35% by weight propylene glycol and 15% by weight ethanol.

Next, a hydroxy cellulose ingredient is added to the steroid/solvent formulation. Hydroxypropyl cellulose or hydroxypropyl methylcellulose, preferably the latter, is added in an amount of from about 0.5% to about 5.0%, preferably from about 0.5% to about 3.0% by weight, depending on the viscosity of the cellulose ingredient. Typically, about 1.5% by weight of a hydroxypropyl methylcellulose having a viscosity of from about 80 to 120,000 centipoises is used. Polyethylene Glycol 4000 or other suitable stiffening agents known to the pharmacist's art may be included, typically 1% to 2% by weight of Polyethylene Glycol 4000 may be added.

The neomycin salt (typically, the hydrochloride or sulfate salt, preferably the sulfate salt) is dissolved separately in water and added to the mixture containing the steroid. From about 0.25% to about 1% by weight, preferably about 0.5% by weight of the neomycin salt is included in the composition of this invention. In order to form a clear gel, from about 0.5% to about 3% by weight, preferably about 1% by weight, of an alkali metal chloride salt, such as sodium or potassium chloride, is added to the steroid/neomycin salt gel composition. The pH of the final clear gel composition may be adjusted, if necessary, to 4.0 to 5 with an acid, typically hydrochloric acid.

The resulting gel is substantially clear, has a substantially uniform consistency and is further characterized by the fact that it is self-preserving in that there is no need to include in the composition the usual preservatives such as the parabens. However, in order to prevent oxidation a small amount, such as 0.1% by weight, of a suitable antioxidant, such as sodium bisulfite and chelating agents, may be optionally included in the composition.

When a composition produced in accordance with the foregoing process is assayed, not only is the neomycin not inactivated but also the steroid is totally available.

In order to further illustrate the practice of this invention, the following examples are included:

EXAMPLE 1

A gel containing 0.025% by weight of betamethasone 17-benzoate and 0.35% by weight neomycin base (present as 0.5% neomycin sulfate) is prepared from the following ingredients:

| % | Ingredients | 1000.00 g |
|---|---|---|
| .025 | 1. Betamethasone 17-benzoate | *0.2625 |
| .35*** | 2. Neomycin sulfate USP, adjust according to assay or about | 5.00 g |
| | 3. Hydroxypropyl methylcellulose | 15.00 g |
| | 4. Propylene glycol USP | 350.00 g |
| | 5. Alcohol USP | **166.67 g |
| | 6. Polyethylene glycol 4000 USP | 10.00 g |
| | 7. Disodium Edetate USP | 1.00 g |
| | 8. Sodium Bisulfite USP | 1.00 g |
| | 9. Sodium Chloride USP granular | 10.00 g |
| | 10. Hydrochloric Acid N/1 q.s. or about | 3.00 m |
| | 11. Water, Purified USP q.s. to | 1000.00 g |

*5% excess for processing losses
**11% excess for manufacturing losses
***Neomycin base The gel is prepared by dissolving betamethasone 17-benzoate in the alcohol and propylene glycol employing a suitable mixer. To this is added the hydroxypropyl methylcellulose. It is mixed until the methylcellulose is wetted.

In a separate vessel neomycin sulfate is mixed together with polyethylene glycol 4000, the disodium edetate and sodium bisulfite and approximately 400 grams of water. When the solution is complete, it is added to the betamethasone 17-benzoate solution. The sodium chloride dissolved in approximately 40 grams of water is added to the resulting mixture. With mixing, the pH is then adjusted with hydrochloric acid to about 4.0 to 5.0. Sufficient water is added to make 1000 grams. There is obtained a clear gel containing 0.025% by weight of betamethasone 17-benzoate and 0.35% by weight of neomycin (present as 0.5% neomycin sulfate).

EXAMPLE 2

Employing the procedure described in Example 1 by substituting fluocinolone acetonide for betamethasone 17-benzoate, a clear gel is also obtained.

EXAMPLE 3

Employing the procedure described in Example 1, by substituting betamethasone 17-valerate for betamethasone 17-benzoate, a clear gel is also obtained.

EXAMPLE 4

The biological activity of the gel produced in accordance with Example 1 is compared with an aqueous solution of neomycin sulfate. The test procedure utilized is the agar cup method utilizing *S. aureus* ATCC 6538P as the test organism. The following results were obtained:

| Formulation | Zone of Inhibition (mm)* | Neomycin Base (mcg/ml) | Zone of Inhibition (mm)* |
|---|---|---|---|
| Composition of Example 1 | 8.6 | 3,500 | 8.0 |
| Placebo | N.Z.** | 3,000 | 7.8 |
| | | 2,500 | 7.4 |
| | | 2,000 | 7.1 |
| | | 1,000 | 6.7 |
| | | 500 | 5.9 |
| | | 250 | 5.2 |
| | | 125 | 4.2 |
| | | 60 | 3.0 |
| | | 30 | 2.6 |
| | | 15 | 2.3 |
| | | 10 | 2.1 |

*Average of two observations
**No zone

The placebo utilized in the above test comprises all the ingredients except neomycin and betamethasone 17-benzoate. The above results show that utilizng the process of this invention the neomycin sulfate retains its antimicrobial activity as the zone of inhibition approximates the zone of inhibition produced by an aqueous solution of neomycin sulfate.

EXAMPLE 5

In order to illustrate the clinical effectiveness of the composition, a double blind study involving 10 normal adults was made. The two preparations labeled A and B were applied to the volar aspects of the forearms of 10 patients in random fashion, three applications of each preparation being made to each patient.

The arms were then covered for 20 hours and the areas were then read 1 hour and 8 hours after the removal of the covering.

Blanching of an area, i.e., vasoconstriction was regarded as positive, i.e., absorption of the steroid had occurred. The results obtained were as follows:

| | TOTAL NO. OF APPLICATIONS | NUMBERS WITH POSITIVE BLANCHING | |
|---|---|---|---|
| | | 1 Hour | 8 Hours |
| GEL A | 30 | 23 | 27 |
| GEL B | 30 | 19 | 24 |

Summary:
After 20 hours of the patients receiving preparation A:
    23 showed positive
    7 showed negative
    27 showed positive
    3 showed negative

SUMMARY:

After 20 hours of the patients receiving preparation A:
    23 showed positive
    7 showed negative
    27 showed positive
    3 showed negative After 20 hours of the patients receiving preparation B:
    19 showed positive
    11 showed negative
    24 showed positive
    6 showed negative Preparation A utilized in the above test contained betamethasone 17-benzoate in a gel formulation previously known. Preparation B was prepared in accordance with the process of Example 1.

From the foregoing results, it is clearly shown that in utilizing the present process the addition of neomycin did not inactivate or interfere with the absorption of the steroid.

We claim:

1. A stable aqueous clear gel composition comprising about 0.02625% by weight of betamethasone 17-benzoate about 0.5% by weight of neomycin sulfate, about 35% by weight propylene glycol, about 16.67% by weight ethanol, about 1.5% by weight of hydroxypropyl methylcellulose having a viscosity of from about 80 to about 120,000 centipoises, about 1% by weight of sodium chloride and a sufficient amount of 1N hydrochloric acid to adjust the pH of the composition to about 4.0 to 5.0.

* * * * *